United States Patent [19]
Wallach et al.

[11] Patent Number: 5,766,917
[45] Date of Patent: Jun. 16, 1998

[54] METHOD FOR IDENTIFYING AND PRODUCING A PROTEASE CAPABLE OF CLEAVING THE TNF RECEPTOR

[75] Inventors: David Wallach, Rehovot, Israel; Cord Brakebusch, Brunswick, Germany; Eugene Varfolomeev; Michael Batkin, both of Rehovot, Israel

[73] Assignee: Yeda Research and Development Co. Ltd., Rehovot, Israel

[21] Appl. No.: 837,941

[22] Filed: Apr. 28, 1997

Related U.S. Application Data

[62] Division of Ser. No. 321,668, Oct. 12, 1994, Pat. No. 5,669,859.

[30] Foreign Application Priority Data

Oct. 12, 1993 [IL] Israel ......................................... 107268

[51] Int. Cl.$^6$ .................................. C12N 9/50; C12N 9/64
[52] U.S. Cl. ........................... 435/219; 435/226; 530/350; 530/327; 530/328
[58] Field of Search ...................... 435/219, 226; 530/350, 327, 328

[56] References Cited

FOREIGN PATENT DOCUMENTS 0568925  11/1993  European Pat. Off. .

OTHER PUBLICATIONS

Angelo, et al, "Elastatinal, A–PMSF, and pepstatin inhibit p80 tumor necrosis factor receptor (TNF–R) shedding in activated human lymphocytes", *Proceedings of the American Association for Cancer Research*; 34:441 (1993).

Ehlers, et al, "Membrane Proteins with Soluble Counterparts: Role of Proteolysis in the Release of Transmembrane Proteins", *Biochemistry*; 30(42):10065–10074 (1991).

Gary, et al, "Cloning of human tumor necrosis factor (TNF) receptor cDNA and expression of recombinant soluble TNF– binding protein", *Proceedings of the National Academy of Sciences of the USA*; 80(10):7380–7384 (1990).

Gullberg, et al, "Involvement of an Asn/Val cleavage site in the production of a soluble form of a human tumor necrosis factor (TNF) receptor. Site–directed mutagenesis of a putative cleavage site in the p55 TNF receptor chain"; *European Journal of Cell Biology*; 58:307–312 (1992).

Heimbach, et al, "Affinity purification of the HIV–1 protease", Chemical Abstracts; 112(7)(51017):51022(1990).

Hwang, et al, "A 20 amino acid synthetic peptide f a region from the 55 kDa human TNF receptor inhibits cytolytic and binding activities of recombinant human tumour necrosis factor in vitro", *Proc. R. Soc. Lond. B*; 245:115–119 (1991).

Porteu, et al, "Human Neutrophil Elastase Releases a Ligand–binding Fragment from the 75–kDa Tumor Necrosis Factor (TNF) Receptor", *The Journal of Biological Chemistry*; 266(28): 18846–18853 (1991).

*Primary Examiner*—Rebecca E. Prouty
*Attorney, Agent, or Firm*—Browdy and Neimark

[57] ABSTRACT

Molecules which influence the shedding of the cell-bound p55 Tumor Necrosis Factor receptor (p55-TNF-R), are provided, together with methods of producing them.

9 Claims, 10 Drawing Sheets

FIG. 1A

```
  1 CGGCCCAGTCTGATCTTGA                                                                                                 17
 18 ACCCCAAGGCCAGAACTGGAGCCTCAGTCCAGAGAATTCTGAGAAATTAAGCAGAGAGGAGGGAGAGATCACTGGGACCCGTGATCTCTCAACCCTCAA              136
137 CTGTCACCCCAAGGCACTGGGACGTCCTGGACAGACCCAGTCCCGGGAAGCCGCCCACACTGCCCATGCCCTGAGCCCAAATGGGGAGTGAGAGCCATAGCTGTCTGGC    255

Met Gly Leu Ser Thr Val Pro Asp Leu Leu Pro Leu Val Leu Glu Leu Leu Val Gly Ile Tyr Pro Ser Gly Val Ile Gly Leu  345
256 ATG GGC CTC TCC ACG GTG CCT GAC CTG CTG CCG CTG GTG CTG GAG CTG CTG GTG GGA ATA TAC CCC TCA GGG GTT ATT GGA CTG

Val Pro His Leu Gly Asp Arg Glu Lys Arg Asp Ser Val Cys Pro Gln Gly Lys Tyr Ile His Pro Gln Asn Asn Ser Ile Cys Cys Thr  435
346 GTC CCT CAC CTA GGG GAC AGG GAG AAG AGA GAT AGT GTG TGT CCC CAA GGA AAA TAT ATC CAC CCT CAA AAT AAT TCG ATT TGC TGT ACC

Lys Cys His Lys Gly Thr Tyr Leu Tyr Asn Asp Cys Pro Gly Pro Gly Gln Asp Thr Asp Cys Arg Glu Cys Glu Ser Gly Ser Phe Thr  525
436 AAG TGC CAC AAA GGA ACC TAC TTG TAC AAT GAC TGC CCA GGG CCG GGG CAG GAT ACG GAC TGT AGG GAG TGC GAG AGC GGC TCC TTC ACC

Ala Ser Glu Asn His Leu Arg His Cys Leu Ser Cys Ser Lys Cys Arg Lys Glu Met Gly Gln Val Glu Ile Ser Ser Cys Thr Val Asp  615
526 GCT TCA GAA AAC CAC CTC AGA CAC TGC CTC AGC TGC TCC AAA TGC CGA AAG GAA ATG GGT CAG GTG GAG ATC TCT TCG ACA GTG GAC

Arg Asp Thr Val Cys Gly Cys Arg Lys Asn Gln Tyr Arg His Tyr Trp Ser Glu Asn Leu Phe Gln Cys Phe Asn Cys Ser Leu Cys Leu  705
616 CGG GAC ACC GTG TGT GGC TGT AGG AAG AAC CAG TAC CGG CAT TAT TGG AGT GAA AAC CTT TTC CAG TGC TTC AAT TGC AGC CTC TGC CTC

Asn Gly Thr Val His Leu Ser Cys Gln Glu Lys Gln Asn Thr Val Cys Thr Cys His Ala Gly Phe Phe Leu Arg Glu Asn Glu Cys Val  795
706 AAT GGG ACC GTG CAC CTC TCC TGC CAG GAG AAG CAG AAC ACC GTG TGC ACC TGC CAT GCA GGT TTC TTT CTA AGA GAA AAC GAG TGT GTC

Ser Cys Ser Asn Cys Lys Lys Ser Leu Glu Cys Thr Lys Leu Cys Leu Pro Gln Ile Glu Asn Val Lys Gly Thr Glu Asp Ser Gly Thr  885
796 TCC TGT AGT AAC TGT AAG AAA AGC CTG GAG TGC ACG AAG TTG TGC CTA CCC CAG ATT GAG AAT GTT AAG GGC ACT GAG GAC TCA GGC ACC
```

FIG. 1B

```
     Thr (Val Leu Pro Leu Val Ile Phe Gly Leu Leu Ser Leu Leu Phe Ile Gly Leu Met Tyr Arg Tyr) Gln Arg Trp Lys
886  ACA GTG CTG CCC CTG GTC ATT TTC GGT CTT CTT TCC CTC CTC TTC ATT GGT TTA ATG TAT CGC TAC CAA CGG TGG AAG   975

Ser Lys Leu Tyr Ser Ile Val [Cys] Gly Lys Ser Thr Pro Glu Lys Gly Glu Gly Leu Glu Gly Thr Thr Lys Pro Leu Ala Pro Asn
976  TCC AAG CTC TAC TCC ATT GTT TGT GGG AAA CCT TCG ACA CCT GAA AAA GAG GGG GAG CTT GAA GGA ACT ACT ACT AAG CCC CTG GCC CCA AAC  1065

Pro Ser Phe Ser Pro Thr Pro Leu Gly Phe Ser Pro Val Pro Ser Ser Phe Thr Ser Ser Thr Tyr Thr
1066 CCA AGC TTC AGT CCC ACT CCA GGC TTC AGT CCC GTG CCC AGT TCC TTC ACC AGC TCC ACC TAT ACC  1155

Pro Gly Asp [Cys] Pro Asn Phe Ala Ala Pro Arg Arg Glu Val Ala Pro Pro Tyr Gln Gly Ala Asp Pro Ile Leu Ala Thr Ala Leu Ala
1156 CCC GGT GAC TGT CCC AAC TTT GCG GCT CCC CGC AGA GAG GTG GCA CCA CCC TAT CAG GGC GCT GAC CCC ATC CTT GCG ACA GCC CTC GCC  1245

Ser Asp Pro Ile Pro Asn Pro Leu Gln Lys Trp Glu Asp Ser Ala His Lys Pro Gln Ser Leu Asp Thr Asp Pro Ala Thr Leu Tyr
1246 TCC GAC CCC ATC CCC AAC CCC CTT CAG AAG TGG GAG GAC AGC GCC CAC AAG CCA CAG AGC CTA GAC ACT GAC CCC GCG ACG CTG TAC  1335

Ala Val Val Glu Asn Val Pro Pro Leu Arg Trp Lys Glu Phe Val Arg Arg Leu Gly Leu Ser Asp His Glu Ile Asp Arg Leu Glu Leu
1336 GCC GTG GTG GAG AAC GTG CCC CCG TTG CGC TGG AAG GAA TTC GTG CGG CGC CTA GGG CTG AGC GAC CAC GAG ATC GAT CGG CTG GAG CTG  1425

Gln Asn Gly Arg [Cys] Leu Arg Glu Ala Gln Tyr Ser Met Leu Ala Thr Trp Arg Arg Pro Arg Glu Ala Thr Leu Glu Leu
1426 CAG AAC GGG CGC TGC CTG CGG GAG GCG CAA TAC AGC ATG CTG GCC ACC TGG AGG CGG CCC CGG GAG GCC ACG CTG GAG CTG  1515
```

FIG. 1C

```
     Leu Gly Arg Val Leu Arg Asp Met Asp Leu Leu Gly Cys Leu Glu Asp Ile Glu Glu Ala Leu Cys Gly Pro Ala Ala Leu Pro Pro Ala
1516 CTG GGA CGC GTG CTC CGC GAC ATG GAC CTG CTG GGC TGC CTG GAG GAC ATC GAG GAG GCG CTT TGC GGC CCC GCC CTC CCG CCC GCG  1605

Pro Ser Leu Leu Arg End
1606 CCC AGT CTT CTC AGA TGA GGCTGCGCCCTGCGGGCAGCTCTAAGGACCGTCCTGCGAGATCGCCTTCCAACCCCACTTTTTCTGGAAAGGAGGGGTCCTGCAGGGCAAGCA  1718
             *
1719 GGAGCTAGCAGCCGCCTACTTGGTGCTAACCCCTCGATGTACATAGCTTTTCTCAGCTGCCTGCGGCGCCGACAGTCAGCGCTGTGCGCGCGGAGAGAGGTGCGCCGTGGCTCAAG  1837
1838 AGCCTGAGTGGGTGGTTTGCGAGGATGAGGACGCTATGCCTCCTCCGTTTGGGTGTCCCTCCACCAGCAAGGCTGCTCGGGGCCCCTGGTTCGTCCCTGAGCCTTTTCACAGTGC   1956
1957 ATAAGCAGTTTTTTTTGTTTTGTTTTGTTTTGTTTTGTTTTAAATCAATCATGTTACACTAATAGAAACTTGGCCACTCCTGTGCCCTCCTGCCTGGACAAGCACATAGCAAGCTGAAC  2075
2076 TGTCCTAAGGCAGGGCGAGCACGGAACAATGGGCCTTCAGCTGTGGACTTTTGTACATAAAATTCTGAAGTTAAAAAAAAAAAAA  2175
```

FIG. 2

| | hu p55 TNF-R | mu EGF-R | PMA induced cleavage |
|---|---|---|---|
| C3 | K L C L P | S F  E V W P S G P K I P S (I A T) | − |
| C4 | K L C L P | S F  (F A T) | − |
| C5 | K L C L P Q I E N V K G T E D S G T | S F  E V W P S G P K I P S (I A T) | + |
| C6 | K L C L P Q I E N V K G T E D S G T | S F  (F A T) | + |
| C9 | C H L C H A N C T Y G C A G P G L Q | G C  E V W P S G P K I P S (I A T) | − |
| hu p55 TNF-R | K L C L P Q I E N V K G T E D S G T | T (T V L L) | + |

C-Termini on the soluble form    Transmembranal region

FIG. 5

```
I E N V K G T E D S G T T (V)    Wild type
        ↑   ↑

G T T (V)    Δ 170-179
        G T E D S G T T (V)    Δ 170-174
I E N V K       G T T (V)    Δ 175-179

I       V K G T E D S G T T (V)    Δ 171-172
I E       K G T E D S G T T (V)    Δ 172-173
I E N       G T E D S G T T (V)    Δ 173-174
I E N V       T E D S G T T (V)    Δ 174-175
I E N V K       E D S G T T (V)    Δ 175-176
I E N V K G       D S G T T (V)    Δ 176-177
I E N V K G T       S G T T (V)    Δ 177-178
I E N V K G T E       G T T (V)    Δ 178-179
I E N V K G T E D       T T (V)    Δ 179-180
I E N   K G T E D S G T T (V)    Δ 173

I Ⓐ N V K G T E D S G T T (V)    E 171 A
I E Ⓐ V K G T E D S G T T (V)    N 172 A
I E N Ⓐ K G T E D S G T T (V)    V 173 A
I E Ⓐ Ⓐ K G T E D S G T T (V)    NV 172-173 AA
I E N V Ⓐ G T E D S G T T (V)    K 174 A
I E N V K Ⓐ T E D S G T T (V)    G 175 A

I E Ⓟ V K G T E D S G T T (V)    N 172 P
I E N Ⓟ K G T E D S G T T (V)    V 173 P
I E N V Ⓟ G T E D S G T T (V)    K 174 P
I E N V K Ⓟ T E D S G T T (V)    G 175 P
I E N V K P Ⓟ E D S G T T (V)    T 176 P
I E N V K P T Ⓟ D S G T T (V)    E 177 P

I E Ⓔ V K G T E D S G T T (V)    N 172 E
I E Ⓓ V K G T E D S G T T (V)    N 172 D
I E Ⓗ V K G T E D S G T T (V)    N 172 H
I E Ⓘ V K G T E D S G T T (V)    N 172 I

I E N Ⓓ K G T E D S G T T (V)    V 173 D
I E N Ⓖ K G T E D S G T T (V)    V 173 G
I E N Ⓡ K G T E D S G T T (V)    V 173 R

I E N V Ⓔ G T E D S G T T (V)    K 174 E
I E N V Ⓠ G T E D S G T T (V)    K 174 Q
I E N V Ⓣ G T E D S G T T (V)    K 174 T
```

METHOD FOR IDENTIFYING AND PRODUCING A PROTEASE CAPABLE OF CLEAVING THE TNF RECEPTOR

CROSS-REFERENCE TO RELATED APPLICATIONS

The present application is a division of copending parent application Ser. No. 08/321,668, filed Oct. 12, 1993 now U.S. Pat. No. 5,665,859.

FIELD OF THE INVENTION

The present invention relates to molecules which influence shedding of the cell-bound p55 Tumor Necrosis Factor receptor (p55 TNF-R), and to their preparation. More particularly, the invention relates to proteases which cleave the cell-bound p55 TNF-R thus creating the soluble receptor, to methods of preparing them, and to their use.

BACKGROUND OF THE INVENTION

It is known that many cell-surface proteins occur also in soluble forms. Some of these soluble molecules are created as such in vivo from distinct mRNAs, transcribed by alternative splicing mechanisms from the same genes which encode the cell-surface proteins. Others are derived from the cell-surface proteins presumably by proteolytic cleavage or, in the case of lipid anchored proteins, by the cleavage of their lipid anchor. Shedding of cell-surface proteins may occur spontaneously and, for example cancer cells seem to have a propensity for doing so. Shedding may also be induced by various stimulating agents.

Knowledge of the mechanisms involved in the shedding of cell-surface proteins and in its regulation is quite limited. None of the proteases or lipases taking part in it have so far been identified. There is also no clear indication of the subcellular site at which it occurs—on the cell surface or within some other intracellular compartment such as the lisozomes to which the cell-surface proteins are transported.

We have now been able to shed light on the mechanisms by which a cell surface protein which serves as a receptor for a cytokine, the p55 TNF receptor, is shed by cells. There are two distinct receptors, the p55 and p75 receptors, by which TNF, a cytokine produced primarily by mononuclear phagocytes, initiates its multiple effects on cell function. Both receptors are expressed in many cell types yet in differing amounts and proportions. The variation in their amounts seems to affect significantly the nature and intensity of the cellular response to TNF. One of the ways by which their expression is regulated is through induced shedding of the receptors. They can be shed in response to different kinds of inducing agents, depending on the type of cells. Granulocytes, for example, shed both receptors in response to the chemotactic peptide—fMLP (formylmethionylleucylphenylalanine) shed specifically their p75 receptor when treated by TNF, while in T lymphocytes shedding of the p75 receptor, which is the predominant TNF receptor species in these cells, occurs upon antigen stimulation.

Shedding of both receptors may also effectively be induced by PMA (phorbol myristate acetate), by the serine phosphate inhibitor okadeic acid and by the calcium ionophore-A23187. The effect of PMA could be shown to reflect activation of protein kinase C, while the effect of okadeic acid seemed to involve the function of some other serine kinase. The amino acid sequences of the soluble forms of the two receptors which had been isolated from urine, correspond to sequences of a cysteine-rich module which extends along a major part of the extracellular domain of the two cell surface receptors. The C terminus of the urine-derived soluble form (Nophar Y., et al., EMBO J., Vol. 9, No.10, pp. 3269–3278 (1990)) of the p55 receptors was initially defined as Asn 172 which is located 11 residues upstream to the transmembranal domain of this receptor, while the C terminus of the soluble form of the p75 receptor corresponds to the residue located 44 amino acid upstream to the transmembranal domain of this receptor. However it was later revealed, that in urine also a somewhat longer soluble form of the p55 receptor, extending two further amino acids downstream towards the intracellular domain exists (Wallach D., et al., Tumor Necrosis Factor III, (Eds. T. Osawa and B. Bonavida) S. Karger Verlag (Basel) pp47–57 (1991). Whether these C termini correspond to the sites at which the receptor had initially been shed upon its release from the cell surface, or reflects also some further cleavage of the soluble form, occurring in the serum or the urine, is yet unknown.

Besides the impact of the shedding of the TNF receptors on the amounts of the cell-surface expressed receptors, this process also seems to contribute to the control of TNF function through effects of the soluble forms of the receptors, which maintain the ability to bind TNF and in doing so can affect its function in two, practically opposing, manners. On the one hand they inhibit the function of TNF by competing for it with the cell-surface receptors but, on the other hand, have also a stabilizing effect on TNF and can thus prolong its effects. The soluble forms of both species of the TNF receptor occur in human serum at concentrations which are normally very low, yet increase dramatically in various disease states, apparently due to enhanced receptor shedding, reaching levels at which they can effectively modulate TNF function.

To gain knowledge of the mechanisms of shedding of the TNF receptors we are attempting to identify the structural elements within the receptors which are involved in their cleavage. Previously we examined the effect of cytoplasmic deletions on the function and shedding of the p55-TNF-R. We found that the signaling activity of the receptor depends on some function(s) of the C terminal part of the intracellular domain. However its shedding and the enhancement of the shedding by PMA occurs even in the complete absence of this domain (Brakebusch C., et al., EMBO J., Vol 11, pp. 943–950 (1992)).

SUMMARY OF THE INVENTION

The present invention provides a protease which is capable of cleaving the soluble TNF-R from the cell-bound TNF-R.

Preferably, the TNF-R is p55 TNF-R.

The invention also provides a method for preparing a protease capable of cleaving the soluble TNF-R from the cell-bound TNF-R, comprising:

a) preparing a construct comprising an amino acid sequence inhibiting the protease, b) affixing said construct to an affinity chromatography column, c) passing a biological sample containing the protease through the column, and d) recovering the protease from the column.

After isolation the protease is purified by conventional methods.

In one embodiment the above construct is prepared by known recombinant methods.

In another embodiment the construct comprises a synthetic peptide.

The invention also provides an antibody to the protease according to the invention which is capable of binding to the protease and either neutralizes the enzymatic activity of the protease or prevents the protease from binding to the receptor.

Such an antibody may either be polycolonal or monoclonal, and may be either murine or human, and may be prepared in a conventional manner.

The invention also provides a method for enhancing soluble TNF-R function, comprising administering an effective amount of a protease according to the invention to a patient.

In another aspect the invention provides a method for enhancing TNF function comprising administering an effective amount of an antibody according to the invention to a patient.

The invention also provides inhibitors of proteases comprising any of the following constructs depicted in FIG. 5:

a) Δ 172–173
b) Δ 173–174
c) Δ 174–175
d) Δ 173
e) V 173 P
f) K 174 P
g) G 175 P
h) V 173 D
i) V 173 G

Such inhibitors may also be muteins of the above constructs.

The invention also provides a DNA molecule comprising a nucleotide sequence encoding the protease capable of cleaving the soluble TNF-R from the cell-bound TNF-R.

A transformant host cell transformed with the replicable expression vehicle encoding the protease of the invention, which expression vehicle may be either prokaryotic or eukaryotic, also forms part of the present invention.

The protease in accordance with the invention is produced recombinantly by culturing a transformant host cell of the invention in a suitable culture medium and isolating the protease.

Pharmaceutical compositions comprising the protease of the invention as active ingredient together with a pharmaceutically acceptable carrier form yet another aspect of the invention.

BRIEF DESCRIPTION OF THE DRAWINGS

FIGS. 1A–1C shows the nucleotide (SEQ ID NO:1) and amino acid sequence (SEQ ID NO:2) of the p55 TNF-R, the transmembranal region being encircled, the cysteines being boxed and the putative glycosylation sites being overlined. The dashed overline indicates the N terminus of the soluble p55 TNF-R and the arrows indicate the major and minor C termini of the soluble p55 TNF-R.

FIG. 2 is a diagrammatic presentation of human p55 TNF-R murine EGF receptor chimeric molecules used for studying the involvement of the transmembranal and intracellular domains of the p55 TNF-R in its shedding. The illustrated sequence for chimera C3 is SEQ ID NO:3; C4 is SEQ ID NO:4; C5 is SEQ ID NO:5; C6 is SEQ ID NO:6; C9 is SEQ ID NO:7. The illustrated partial sequence for hu p55 TNF-R is residues 193–214 of SEQ ID NO:2.

FIG. 5 shows the maps of the various p55 TNF-R mutants tested in the study of the structural requirement for the shedding. The illustrated sequence for the wild type is residues 199–212 of SEQ ID NO:2. The succeeding mutants are SEQ ID NO:8 to SEQ ID NO:42, respectively.

DETAILED DESCRIPTION OF THE INVENTION

Figure 3:
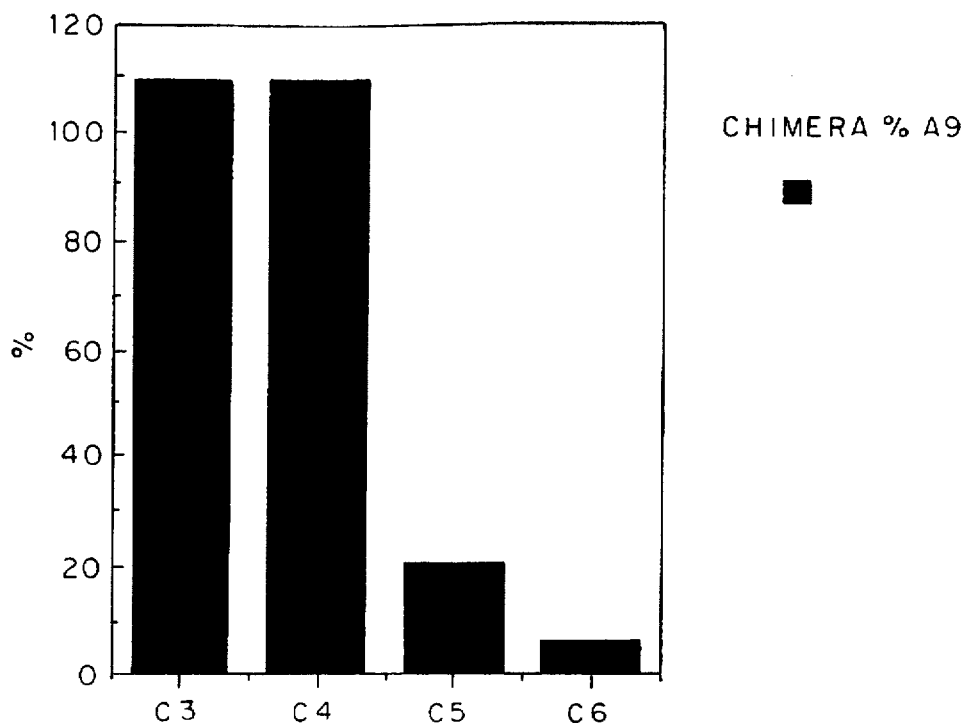
FIG. 3 shows the results of a test of the ability of PMA to induce shedding of the chimeric molecules of FIG. 2, in terms of the ability of the cells expressing them to bind radiolabeled TNF after PMA treatment.

In accordance with the present invention, we have now employed a different approach for determining the role of the different domains in the p55 TNF-R on its shedding. For this purpose we replaced different parts of the p55 TNF-R with the corresponding parts of the EGF-receptor, which is not shed in response to agents inducing the shedding of the p55 TNF-R. Study of the shedding of these chimeric molecules indicated that the shedding and its enhancement by inducing agents are not affected by the structure of those regions in the receptor molecule which are embedded in the cell-both the intracellular, as well as the transmembranal domains, nor by that part of the receptor which is shed, namely the cysteine rich module in its extracellular domain. The only region whose structure affects the shedding is the one located close to what appears to be site of cleavage of the receptor, namely—the spacer region in the extracellular domain which links the cysteine rich module to the transmembranal domain. An attempt to define the structural requirements of the shedding further, by detailed study of the mutations in the spacer region on the shedding revealed a rather complicated dependence of the shedding on the sequence on the basis of which it should be possible to design pharmaceutical agents by which the function of the protease can be controlled.

To elucidate the structural requirements of the shedding of the p55-TNF-Rs, we assessed the effects of various mutations of the receptor on its shedding. In a first stage we aimed at a general idea of the relation of the structural requirements for shedding of the receptor and for its signaling. We therefore expressed the various mutants constitutively in mouse A9 cells, which are sensitive to the cytocidal effect of TNF, and then determined their shedding by these cells. However, since the interclonal variation indigenous to this way or proceeding did not allow a sensitive enough assessment of partial effects of mutations on the shedding of the receptors, it seemed preferable to determine the shedding of the receptor mutants by their transient expression in the monkey COS-7 cells. This transient expression assay obviated also the need for the lengthy isolation of cell clones expressing the transfected receptors.

Although the cells applied in the constitutive and transient expression test systems were different, the shedding of the p55 receptor by them occurred in similar manners and was affected similarly by a series of different mutations. In both test systems, phorbol myristate acetate (PMA), an activator of the serine protein kinase C as well as orthovanadate and, to a larger extent, peroxyvanadate, which facilitates tyrosine kinase effects, caused a marked enhancement of the shedding, manifested in increased rate of appearance of soluble receptors in the cells' growth media concomitantly with a decrease in amounts of the cell surface-expressed receptors. This effect was rapid, reaching a significant extent within less than a minute. Its initial rate was little affected by the protein synthesis blocking agent CHI or ammonium chloride, which inhibits lysozomal activities. A significantly decreased rate of shedding was observed also when the cells were incubated at a low temperature. However, in prolonged incubation some shedding could be observed even at 0° C.

Some shedding of the receptors could be observed also in the absence on any inducing agent. The rate of this spontaneous shedding varied from one receptor mutant to another proportionally to their rates of induced shedding. In the transiently expressing COS-7 cells the rate of spontaneous shedding was rather high, resulting in accumulation of significant amounts of the soluble receptors in the growth media already before application of any inducing agents; it seemed high enough to affect the steady-state level of the cell-surface receptors, as receptors which could be effectively shed were found to be expressed by the COS-7 cells at significantly lower amounts than receptors mutated in a way which decreased their shedding. To account for this difference in expression of the various receptor mutants, we chose to compare the effectivity of shedding of the various mutants by relating to the quantitative ratio of the amount of the soluble receptors which accumulated in the growth media within the shedding induction period and the amount of cell-surface receptors at the start of the induction period.

We have found in accordance with the present invention that shedding of the p55 TNF-R occurs independently of the sequence properties of the intracellular or transmembranal domain of the receptor, or of the structure of that portion of the extracellular domain which is shed. The only region whose amino acid sequence affects the cleavage of the receptor is that in which the cleavage occurs, namely the spacer region which links the cysteine rich module in the extracellular domain with the transmembranal domain. It appears that within this region, not only the residues which are immediately adjacent to the site of cleavage, but also some other residues affect this process.

Shedding of the p55 receptor was induced using agents which enhance protein phosphorylation. The involvement of induced phosphorylation in the induction of this process is likely to account, at least partly, for its energy dependence. Apparently, the shedding can be induced through effects of several different kinases, including protein kinase C (Brakebusch, et al., 1992 see above) another, distinct, serine kinase and, as found now, also tyrosine kinases. However, we observed no clear difference in the way by which mutations in the p55 TNF-R affect the shedding induced by PMA, an activator of protein kinase C, or by pervanadate, which facilitates the activity of tyrosine kinases, suggesting that these different kinases activate a common mechanism of shedding.

The protein whose phosphorylation results in the induction of receptor shedding is unlikely to be the receptor itself.

The fact that the shedding was not prevented by replacing those domains of the p55 TNF-R which are embedded within the cell, with the corresponding parts of the EGF-R, a receptor which is not shed, seems to rule out an involvement of phosphorylation of the receptor, or of any other induced change in it, in the mechanism of shedding. In that respect, there is particular interest in the fact that, beside lack of an effect on the shedding, those regions in the EGF-R molecule which were introduced into the chimera with the p55 TNF-R do not impose receptor uptake, which seems to exclude a role for induced uptake in the shedding. The resistance of the shedding to ammonium chloride and chloroquine, agents known to inhibit degradative processes within intracellular acidic compartments and the fact that some shedding occurred even when incubating the cells at 0° C., which should prevent any uptake of proteins, exclude further a role of receptor uptake in the process. The sequence requirements for the shedding of the p55 TNF-R in the mouse A9 cells and in the monkey COS-7 cells are very similar, perhaps identical, suggesting that the same or similar protease(s) take part in the shedding in these different cells. More specifically, the findings in accordance with the present invention indicate that a short amino acid sequence in the p55 TNF-R is essential and sufficient for its shedding. This sequence is in the so-called spacer sequence between the transmembranal region and the Cys-rich extracellular domain region of the receptor, with the amino acid residues Asn 172, Val 173, Lys 174 and Gly 175, in particular the Val 173, being most important. Interestingly, the shedding of the receptor is generally independent of the side chain identity of the above noted residues, with the exception of a limited dependence on the identity of Val 173 (e.g. replacement of Asn 172, Lys 174 and Gly 175 by Ala) did not adversely effect the shedding of the receptor. However, mutations which change the conformation of the protein (e.g. replacement of any of the above residues with Pro) adversely effected the shedding process. This sequence requirement is quite different from any sequence requirement for the function of known proteases so far described.

Identification and purification of the protease, despite lack of detailed knowledge about its specific biochemical properties can be effected by, e.g. affinity chromatography. For this purpose the constructs shown to act as protease inhibitors are coupled to a conventional affinity chromatography column, i.e. Affi-Gel 10. Other known solid supports such as other agaroses, resins or plastics may be employed.

A variety of biological materials are available as sources of protease activity. These include tissues, cells, or extracts, or fluids associated therewith which preferably, but not necessarily, are of immunological origin. Established cell lines can also be utilized. In general, any cell expressing TNF-Rs can be employed as the source for the protease.

Cells may be used as is in the affinity purification, or may be stimulated to produce higher levels of protease using known activators for the particular cells employed.

A protease according to the invention, or any molecule derived therefrom which augments the activity of the protease may be employed to decrease the amount of cell-bound TNF-Rs and thus protect from over-response to TNF. Thus the proteases according to the invention are indicated for the treatment of diseases caused by an excess of TNF. Qither administered exogenously, or produced endogenously.

Conversely, the protease inhibitors can be used to prevent shedding of the TNF-Rs, e.g. in cases where the beneficial activities of TNF are to be enhanced, e.g. in the treatment of tumor cells by TNF. This will lead to an increase of the effectivity of the antitumor activity.

The invention will now be illustrated by the following non-limiting examples:

General Procedures and Materials a) Construction of p55-TNF-R mutants and p55-TNF-R-EGF-R chimeras The cDNA of the hu-p55-TNF-R (Nophar, Y. et al., EMBO J., Vol. 9, pp.3269–3278 (1990)) was digested with BanII and NheI, resulting in removal of most of the 5' and 3' non-coding sequences. The p55-TNF-R mutants were generated by oligonucleotide-directed mutation, using the "Altered Sites" mutagenesis kit (Promega, Madison, Wis.). The mutations were confirmed by sequencing the regions of interest. Fragments of the hu-p55-TNF-R and of the EGF receptor (EGF-R) cDNAs used for creation of receptor chimeras were produced by PCR, using the 'Vent' DNA polymerase (New England Biolabs, Beverly, Mass.). Some of the chimeras (designated $C_3$, $C_4$, $C_5$ and $C_6$ in FIG. 2), were constructed using mouse EGF-R cDNA (Avivi A., et al., Oncogene, Vol. 6, pp. 673–676 (1991)), kindly provided by Dr. D. Givol of the Weizmann Institute, Rehovot, Israel, and others (e.g. that designated $C_9$ in FIG. 2) were constructed using human EGF-R cDNA (Merlino G. T., et al., Molec. Cell. Biol., Vol. 5, pp. 1722–1734 (1985)), kindly provided by Drs. G. Merlino and I. Pastan, NIH, Bethesda, MD. For constitutive expression of the wild-type or mutated receptors in A9 cells, they were introduced into the eukaryotic expression vector pMPSVEH (Artelt P. et al., Gene, Vol. 68, pp. 213–219 (1988)), kindly provided by Dr. H. Hauser, GBF, Braunschweig, Germany) which contains the myeloproliferative sarcoma virus promoter. For transient expression of the receptors in COS-7 cells, they were introduced into the pEXV1 vector (Miller, J. and Germain, R. N., J. Exp. Med., Vol. 164, pp. 1478–1489 (1986)), which contains the SV40 virus enhancer and early promoter. In all of the hu-p55-TNF-R constructs expressed in COS-7 cells, the receptor was cytoplasmically truncated from residue 207 downstream (in addition to the other specified mutations).

b) Constitutive and transient expression of the wild type and mutant receptors

A9 (Littlefield, J. W., Nature, Vol. 203, pp. 1142–1144 (1964)) and COS-7 (Gluzman, Y., Cell, Vol. 23, pp. 175–182 (1981)) cells were cultured in Dulbecco's Modified Eagle's Medium (DMEM), containing 10% fetal calf serum (FCS), 100 u/ml penicillin and 100 µg/ml streptomycin (growth medium). The A9 cells were transfected with pMPSVEH expression constructs together with the pSV2neo plasmid, and cell colonies constitutively expressing these constructs were isolated as previously described (Brakebusch, C., et al., EMBO J., Vol. 11, pp. 943–950 (1992)). Transient expression of pEXV1 constructs in COS-7 cells was carried out as follows: one day after the COS-7 cells were seeded at 60% cell density they were transfected by applying the DNA of the constructs to them for them for 4 h. at a concentration of 3 µg/ml in DMEM (4 ml/10 cm dish, 10 ml/15 cm dish) containing DEAE dextran (200 µg/ml, Pharmacia, Uppsala, Sweden). The cells were then rinsed with DMEM and incubated for 2 min in PBS (0.154M sodium chloride plus 10 mM sodium phosphate, pH 7.4) containing 1 mM $CaCl_2$, 1 mM $MgCl_2$ and 10% (v/v) DMSO. The cells were rinsed and further incubated for 10 h. in growth medium, then detached by trypsinization and seeded either into 1.5 cm culture plates ($10^5$ cells/plate) or (to assess the shedding of metabolically labeled EGF-R) into 15 cm plates ($1.2 \times 10^6$ cells/plate). Expression and efficacy of shedding of receptors encoded by the transfected constructs were assessed 48 h. later.

c) Determination of binding of TNF and EGF to cells

Recombinant human TNF-α (TNF, $6 \times 10^7$ U/mg of protein, Genentech Co., San Francisco, Calif., kindly provided by Dr. G. Adolf of the Boehringer Institute, Vienna, Austria) was radiolabelled with chloramine T to a specific radioactivity of 500 Ci/mmol (Israel, S., et al., Immunol. Lett., Vol. 12, pp. 217–224 (1986)). EGF (β-urogastrone, Boehringer Mannheim GmbH, Biochemica, Mannheim, Germany) was labeled with [125I] to a specific radioactivity of 300 Ci/mmol, using the IODOGEN reagent (Pierce Chemical Co., Rockford, Ill., U.S.A.), following the instructions of the manufacturer. Binding of radiolabelled TNF and EGF to cells was determined by applying them to the cells on ice at a concentration of 1 nM, either alone or with a 100-fold excess of unlabelled cytokines, as described previously (Brakebusch et al., (1992) supra).

d) Measurement of the shedding of the soluble forms of hu-p55-TNF-R and EGF-R

A9 cells constitutively expressing the transfected constructs were seeded, 24 hrs prior to the assay, into 1.5 cm tissue culture plates at a density of $2.5 \times 10^5$ cells/plate. COS-7 cells expressing transiently transfected constructs were seeded into 1.5 cm tissue culture plates, 48 hrs prior to the assay, as described above. At time zero, some of the plates were placed on ice to determine the binding of radiolabelled TNF or EGF to the cells prior to induction of shedding. The medium in the other plates was replaced with fresh DMEM (200 µl/plate) either without serum (for tests in which PV was the agent used to induce shedding) or with 10% FCS (for the other tests). Unless otherwise indicated, PMA (20 ng/ml) or PV (100 µM, prepared as described in Fantus, I. G., et al., Biochemistry, Vol. 28, pp. 8864–8871 (1989)), was applied to the cells for 1 hr. Application of Chloroquine (50 µg/ml), ammonium chloride (10 mM) or cycloheximide (50 µg/ml) to the cells was done 30 min prior to application of PMA or PV, followed by further incubated with these agents for 20 min after addition of the latter reagents. Upon termination of incubation with the shedding-inducing agents, the plates were transferred to ice to determine the binding of radiolabelled TNF or EGF to the cells. The amounts of the soluble form of the hu-p55-TNF-R in the cells' growth media were determined after centrifugation at 3000 g for 5 min to remove detached cells and cell debris, followed by 5-fold concentration of the media, using the SpeedVac concentrator (Savant, Farmingdale, N.Y.). The determination was performed by two-site capture ELISA, using a mouse monoclonal antibody and rabbit antiserum against this protein, as described (Aderka, D. et al., Cancer Res., Vol. 51, pp. 5602–5607 (1991)).

To assess the formation of the soluble form of the EGF-R, COS-7 cells transfected with the EGF-R constructs ($1.2 \times 10^6$ cells, seeded into 15 cm dishes as described above) were labelled with [35S] methionine by incubation for 10 hrs at 37° C. in DMEM (methionine-free) containing 70 µCi/ml [35S] methionine and 2% dialyzed FCS. The cells were then rinsed and further incubated for 1 hr in growth medium containing PMA (20 ng/ml). The medium was collected, cleared of cell debris by spinning, and then further cleared of proteins that bind nonspecifically to protein A by incubating it twice at 4° C. for 4 hrs with immobilized protein A (Repligen Inc., Cambridge, Mass.; 100 µl/7 ml medium/plate), once alone and once in the presence of 10 µg irrelevant mouse monoclonal antibodies. Immunoprecipitation was then performed by incubation of the medium samples at 4° C. for 2.5 hrs with a monoclonal antibody against the human EGF-R, or, as a control, with a monoclonal antibody against the h-p55-TNF-R, each at 5

µg/sample, followed by further incubation for 2.5 hrs with immobilized protein A (40 µl). The protein A beads were washed three times with PBS containing 0.2% sodium deoxycholate and 0.2% NP-40, and the proteins bound to them were then analyzed by SDS-PAGE under reducing conditions (7.5% acrylamide). Autoradiography was performed after treatment of the gel with the Amplify intensifying reagent (Amersham International plc, Amersham, UK)

e) Presentation of the data

All data on receptor shedding presented in the following Examples 1-3 and their accompanying figures, FIGS. 3, 4 and 6–9, are representative examples of at least four experiments with qualitatively similar results, in which each construct was tested in triplicate. It should be noted that the efficacy of construct expression varied rather extensively (in their constitutive expression among different cell clones, and in their transient expression among different constructs). The data on the extent of shedding have therefore been normalized by relating them to the initial receptor levels in the cells, prior to the induction of shedding. The amounts of cell-surface bound receptors obtained after induction are presented as percentages of their initial amounts (see FIGS. 3, 6 and 8) and hence those forms of the receptors which are shed show a lower percentage of remaining cell-surface receptors than do those forms which are not shed. The amounts of soluble receptors formed as a consequence of the shedding are presented in relative units (see FIGS. 4, 7 and 9), i.e. amount of soluble receptors produced during shedding induction (in pgs) per amount of cells-surface receptors just prior to shedding induction (in $cpm \times 10^3$ of cell bound radiolabelled TNF, and hence those forms of receptors which are shed show higher amounts than those which are not shed. Residue numbering in the h-p55-TNF-R is according to Schall, T. J. et al., Cell, Vol. 61, pp. 361–370 (1990), in the mouse EFG-R according to Avivi, A. et al., (1991) supra, and in the human EGF-R, according to Ulrich, A. et al., Nature, Vol. 309, pp. 418–425 (1984)

EXAMPLE 1

Use of chimeras of the p55 TNF receptor and the EGF-R for assessing the role of different regions in the TNF receptor in its shedding.

Our study of previous work concerning the shedding of cytoplasmic deletion mutants of the p55 receptor indicated that the shedding, and its enhancement by PMA, occur independently of the intracellular domain of the receptor. To explore further the role of the different domains in the receptor in its shedding, we now attempted to replace them with- the corresponding region in a receptor which is not shed. The receptor for the epidermal growth factor (EGF) seemed suitable for that purpose. PMA induces a decrease in expression of this receptor, yet apparently not by its shedding but by induction of uptake of this receptor into the cell. This uptake was related to induced phosphorylation of its intracellular domain. A series of chimeras (see FIG. 2 for various chimeras designated $C_3$, $C_4$, $C_5$, $C_6$ and $C_9$) between the p55 TNF-R and a cytoplasmic deletion mutant of the EGF-R was created and tested for the extent of shedding of chimeras in response to PMA and pervanadate (see General Procedures above). The mutated EGF-R was not shed, nor taken up by cells in response to PMA, nor in response to pervanadate (results not shown). Both agents did induce the shedding of a chimeric receptor comprised of the remaining part of the intracellular and the transmembranal domain of the EGF receptor, and the extracellular domain of the p55 TNF receptor (FIG. 2, chimeras $C_5$ and $C_6$). However, chimeric receptors in which the "spacer" region in the extracellular domain of the p55 TNF-R, which links the cysteine rich module with the transmembranal domain was deleted (FIG. 2, chimeras $C_3$ and $C_4$), or replaced with the corresponding region in the EGF-R (FIG. 2, chimera $C_9$), could not be shed. These findings indicated that the structural requirement for the shedding of the p55 TNF receptor and for its enhancement by PMA and pervanadate are fully confined to the spacer region.

Figure 4:
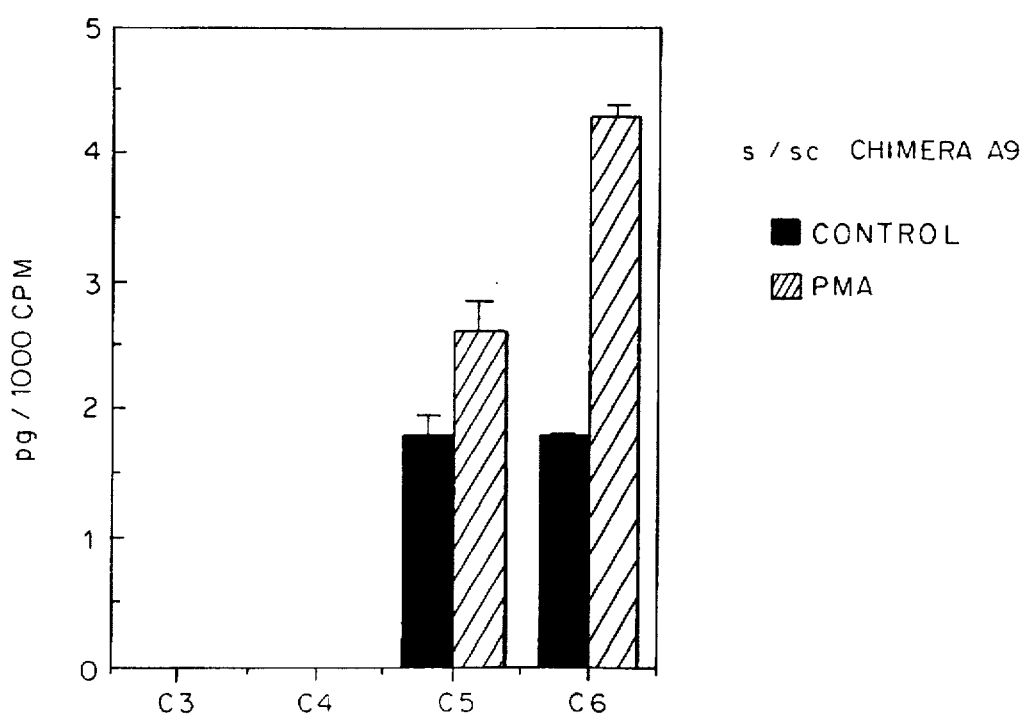
FIG. 4 shows the results of the test as in FIG. 3 in terms of the amount of soluble p55 TNF-R shed by the cells.
Figure 8:
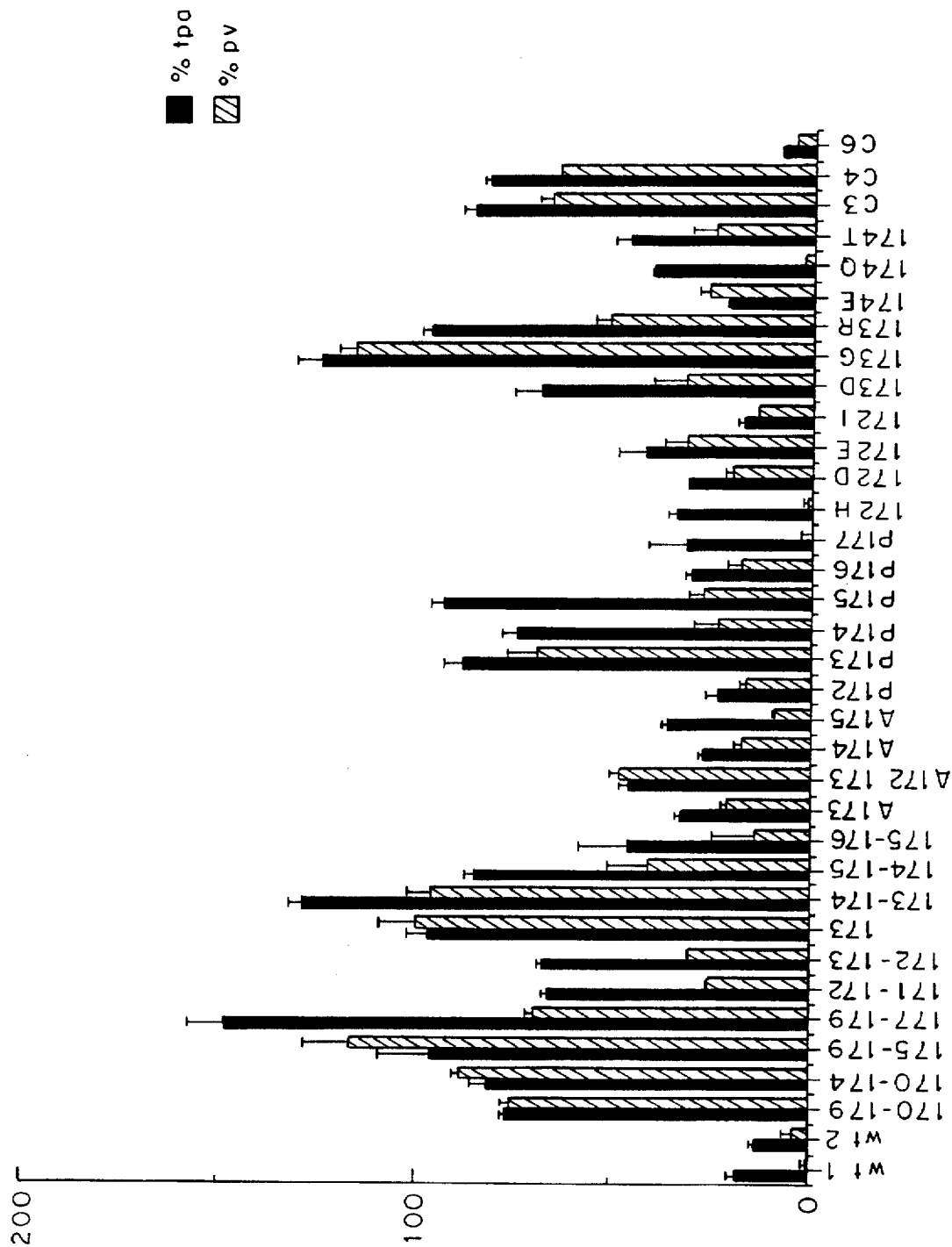
FIG. 8 shows the results of a test of the ability of PMA and pervanadate to induce shedding of some of the mutants of FIGS. 2 and 5, in terms of the ability o f COS-7 cell s expressing them transiently to bind radiolabeled TNF after PMA and pervanadate treatment.
Figure 9:
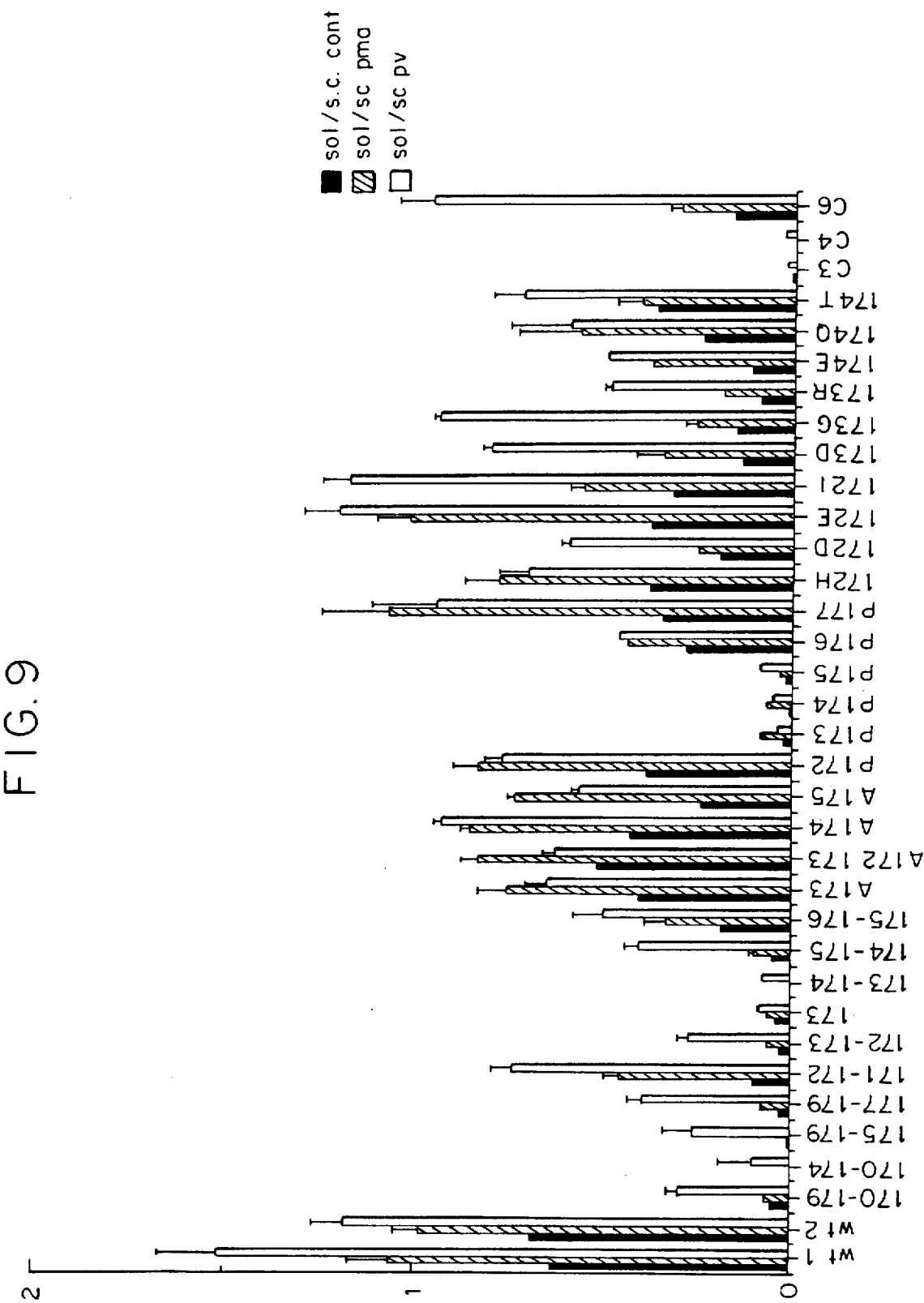
FIG. 9 shows the results of a test of the ability of PMA and pervanadate to induce shedding of some of the mutants of FIGS. 2 and 5, in terms of the amounts of the soluble p55 TNF-R shed by the cell s.

As shown in FIGS. 3 and 4, which present the results of a test of the shedding of p55 TNF/EGF receptor chimeras shown in FIG. 2 expressed constitutively in A9 cells, chimeras which contain the spacer region of the p55 TNF-R (chimeras $C_5$ and $C_6$) are shed while those that do not (chimeras $C_3$ and $C_4$), are not shed in response to PMA. As shown in FIGS. 8 and 9, the same hold true for the shedding of these constructs in response to either PMA of pervanadate (PV) by COS-7 cells which express them transiently.

EXAMPLE 2

Effects of amino acid deletions in the spacer region on the shedding

We have previously found that p55 TNF-R mutants from which most of the spacer region was deleted do not shed spontaneously or in response to PMA (Brakebusch D., et al., Tumor Necrosis-Factor IV (Ed. W. Fiers) S. Karger, Verlag (Basel) pp191–198 (1993)). In order to further define those amino acid residues whose deletion accounted for the lack of shedding of the receptors, we created receptor mutant forms in which various couples of consecutive amino acids within the spacer regions were deleted, and examined their shedding (see General Procedures above). The various deletion mutants studied are presented in the upper part of FIG. 5, where the symbol Δ denotes the deletion and the numeral(s) following the Δ denote the amino acid residue(s) which have been deleted.

As shown in FIGS. 8 and 9, any deletion of two or more amino acids within the spacer region results in some decrease in effectivity of the shedding of the receptor from transiently expressing COS-7 cells in response to PMA or pervanadate. However, the most dramatic decrease in the effectivity occurs in deletion of Val 173 or the couple 173–174. A somewhat less effective decrease was observed in deleting couples 172–173 and 174–175. The data in FIGS. 6 and 7, as to the shedding from cells which constitutively express the receptor mutants show that deletions 172–173 and 173–174 have also dramatic reducing effect on the shedding to the receptor form A9 cells which express them constitutively. These data show that residues 173, 174 and 175 have an important role in determining the specificity of the protease which cleaves the p55 TNF-R. Besides, they imply that also other structural constraints in the spacer region affect its shedding.

EXAMPLE 3

Effects of amino acid replacements in the spacer region on the shedding

Figure 6:
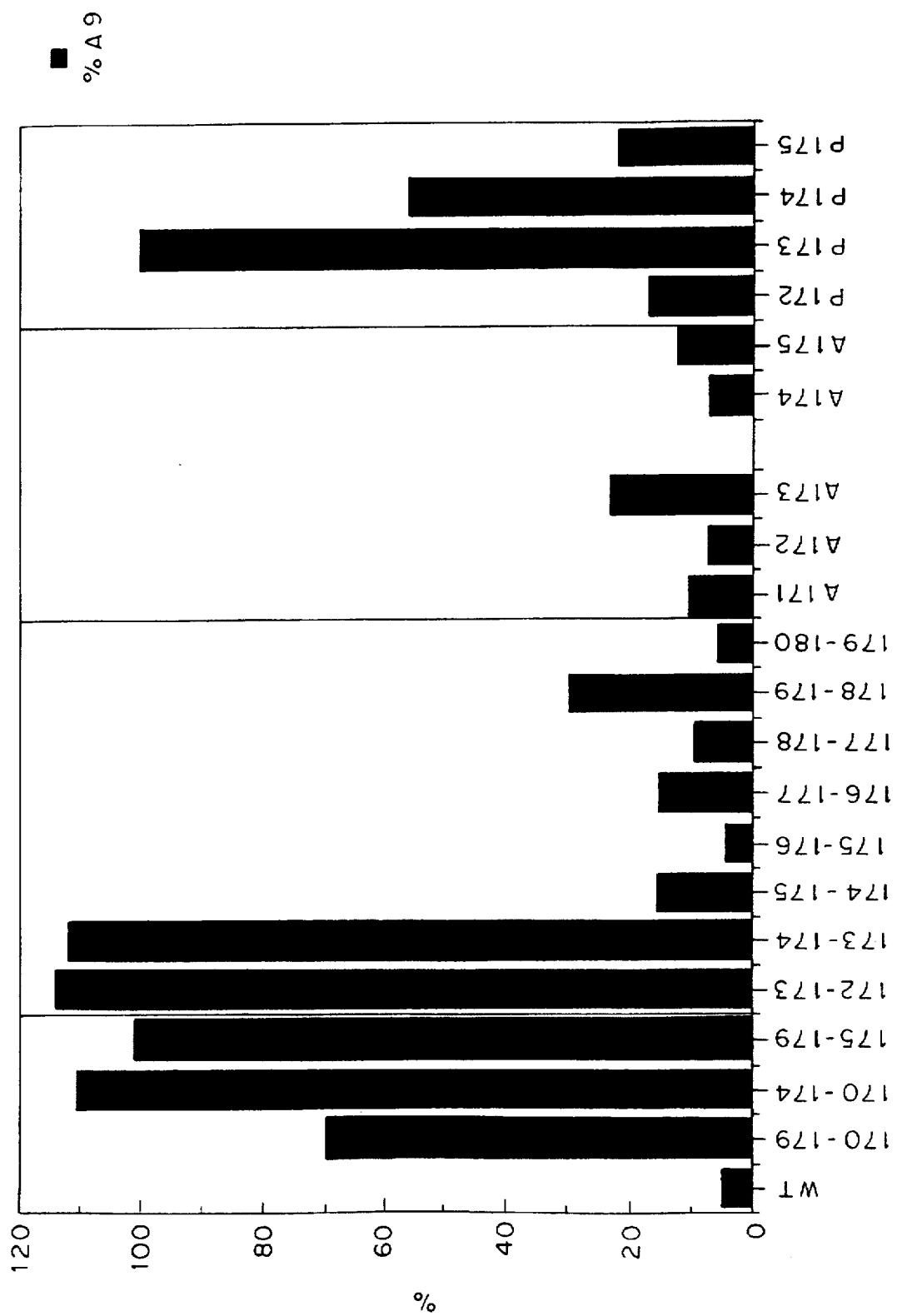
FIG. 6 shows the results of a test of the ability of PMA to induce shedding of some of the mutants of FIG. 5, in terms of the ability of A9 cells expressing them to bin d radiolabeled TNF after PMA treatment.
Figure 7:
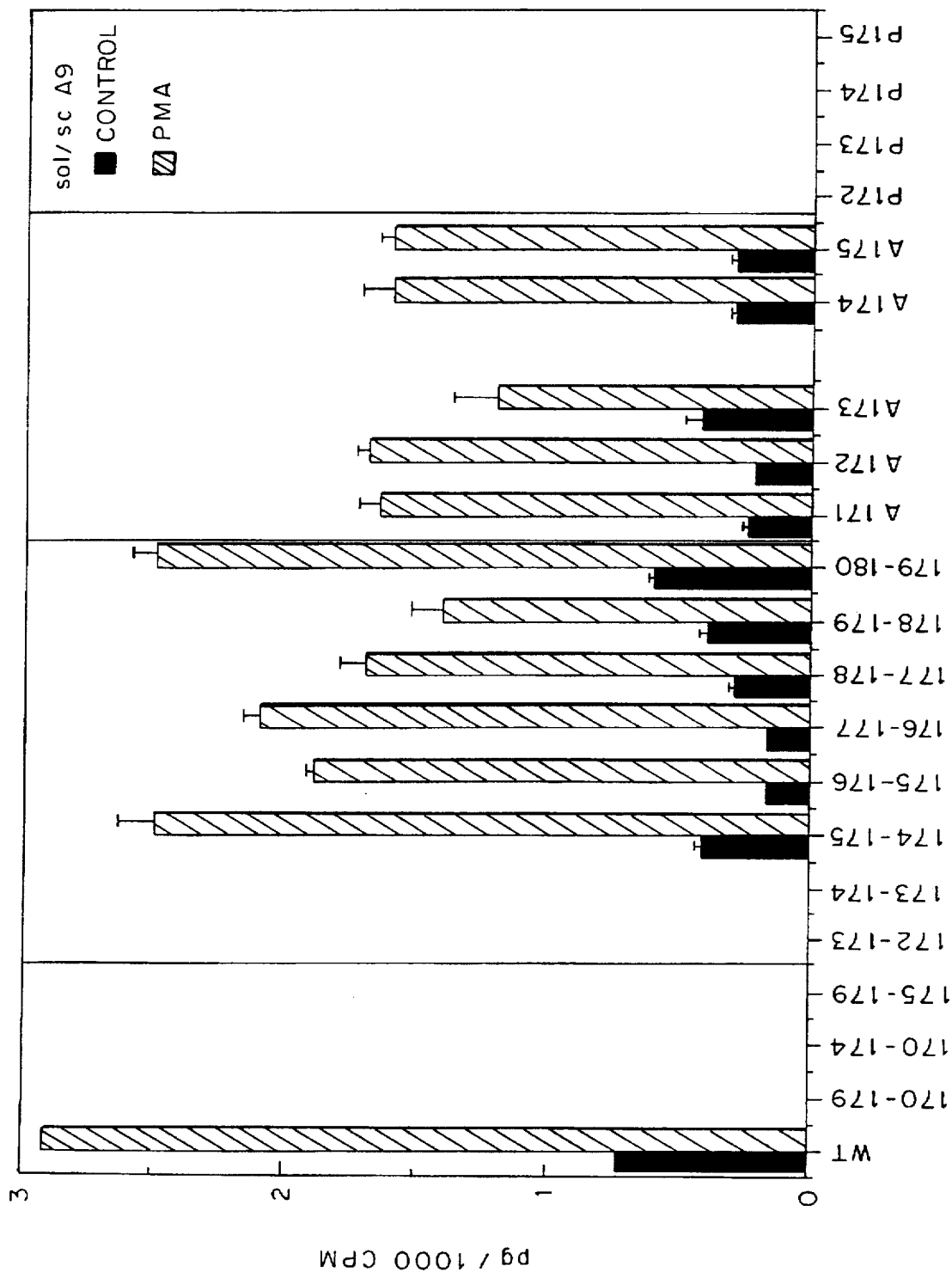
FIG. 7 shows the results of a test of the ability of PMA to induce shedding of some of the mutants of FIG. 5, in terms of the amounts of the soluble p55 TNF-R shed by the cells.

To further define those amino acid residues within the spacer region which affect receptor shedding, we replaced them, one by one, with alanine, (for the alanine replacement mutants, see the mid-section of FIG. 5, where the normally occurring amino acid residue is denoted at the left of the numeral(s) and the alanine (A) replacing that residue is denoted at the right of the numeral, the numeral being the position of the replacement). Assessing the shedding of these mutated receptors, after expressing them constitutively in A9 cells, or transiently in COS-7 cells, failed to reveal an effect of any of these mutations, as is shown in FIGS. 6 and 7 (A9 cells) and in FIGS. 8 and 9 (COS-7 cells), wherein the alanine replacement mutants are denoted by an "A" before the residue number of the replacement.

However replacement of residues 173, 174 and 175 with proline (P) resulted in a drastic decrease of the shedding of the receptors by A9 cells which express them transiently. Moreover, certain other amino acid replacements at the 173 site also resulted in a significant decrease in the effectivity of shedding (FIGS. 6–9). These data implied again that residues 173–175 have an important role in restricting the function of the protease which cleaves the p55 TNF-R (for the proline (P) and other amino acid replacement mutants, see the lower section of FIG. 5, where the denotations of the mutations are a s above).

EXAMPLE 4
Affinity purification of the protease

A peptide whose structure corresponds to that of the spacer region of the TNF-R mutated in such a way that it interferes with its cleavage, yet not with its recognition by the protease, is linked covalently to the resin on an affinity purification column. Detergent extracts of membranes isolated from cells which express the protease capable of cleaving the p55 TNF-R are passed through the column and the unbound material i s washed. Thereafter the protease is eluted, either by increasing the salt concentration or by decreasing the pH, and further purified.

EXAMPLE 5
Antibodies to the protease

Female Balb/C mice (8 weeks old) are injected with 1 μg protease obtained in Example 4 in an emulsion of complete Freund's adjuvant into the hind foot pads, and about three weeks later subcutaneously into the back in incomplete Freund's adjuvant. The other injections are given at weekly intervals, subcutaneously in PBS. Final boosts are given 4 days (i.p.) and 3 days (i.v.) before the fusion in PBS. Fusion is performed using NSO/Mr cells and lymphocytes prepared from both the spleen and the local lymphocytes of the hind legs as fusion partners. The hybridomas are selected in DMEM supplemented with HAT, 15% horse serum and gentamycin 2 μg/ml. Hybridomas that are found to produce antibodies to the protease are subcloned by the limited dilution method and injected into Balb/C mice that were primed with pristane for the production of ascites. Immunoglobulins are isolated from the ascites by ammonium sulfate precipitation (50% saturation) and then dialyzed against PBS containing 0.02% azide. Purity is estimated by analysis on SDS-PAGE and staining with Commassie blue. The isotypes of the antibodies are defined with the use of a commercially available ELISA kit (Amersham, U.K.).

EXAMPLE 6
Affinity purification

Antibodies against the protease can be utilized for the purification of the protease by affinity chromatography, according to the following procedure. The monoclonal antibodies for affinity chromatography are selected by testing their binding capacity for the radiolabeled antigen in a solid phase radio immunoassay. Ascites from all hybridomas are purified by ammonium sulfate precipitation at 50% saturation followed by extensive dialysis against PBS. PVC 96-well plates are coated with the purified McAbs, and after blocking the plates with PBS containing 0.5% BSA, 0.05% Tween 20 (Sigma) and 0.02% NaN$_3$, the wells are incubated with 50,000 cpm $^{125}$I-TNF for 2 h at 37° C., then washed and the radioactivity which binds to each well is quantitated in the gamma-counter. The antibodies with the highest binding capacity are examined for their performance in immunoaffinity chromatography.

Polyacryl hydrazide agarose is used as resin to immobilize the antibodies. The semipurified immunoglobulins are concentrated and coupled as specified by Wilchek and Miron (Methods in Enzymology, Vol 34, pp.72–76 (1979)). Antibody columns of 1 ml bed volume are constructed. Before use, all columns are subjected to 10 washes with the elution buffer, each wash followed by neutralization with PBS. The columns are loaded with the protease obtained in Example 4 in PBS with 0.02%. NaN$_3$. The flow rate of the columns is adjusted to 0.2 to 0.3 ml per minute. After loading, the columns are washed with 50 ml PBS and then eluted with a solution containing 50 mM citric acid, pH 2.5, 100 mM NaCl and 0.02% NaN$_3$. Fractions of 1 ml are collected. Samples of the applied protease, the last portion of the wash (1 ml) and of each elution fraction (8 fractions of 1 ml per column) are taken and tested for protein concentration. All protein measurements are effected according to a microflurescamin method in comparison to a standard solution containing 100 μg BSA/ml (Stein, S. and Moschera, J., Methods Enzymol., Vol. 79, pp.7–16 (1981)).

EXAMPLE 7
Chromatographic purification of the protease

Crude preparations of the protease, obtained by detergent extraction of membranes of cells which express the protease, or partially purified preparations of the protease formed in Example 4 are subjected to a series of chromatographic fractionation steps e.g., based on charge, size, isoelectric point or hydrophobicity of the fractionated proteins. Throughout the fractionation steps the protease activity is followed by determining the ability of the tested fraction to cause cleavage of the p55 TNF-R or of a peptide derived from it at the same site and by the same sequence requirements as those found for the cleavage of the receptor in cells.

EXAMPLE 8
Cloning of the protease

Cells exhibiting the protease activity (namely—exhibiting inducible shedding of their p55 TNF-R) are mutated by chemical mutagens. Cell mutants deficient in the protease activity are isolated by FACS staining for the p55 TNF-R after induction of the shedding. The sequence of the nucleotides in the p55 TNF-R gene within the mutated cells is examined to confirm that the inability to shed in indeed due to aberration of the cleavage mechanism and not to a mutation in the spacer region in the receptor. The mutant cells are then transfected either with the genomic DNA or with a cDNA library derived from cells which express the protease. Clones of cells which have regained the ability to shed due to the transfection are isolated by FACS analysis as above and the transfected gene which has complemented their defect is isolated. In some of these mutants the transfected gene or cDNA that has complemented the defect is expected to be the gene for the protease.

We claim:

1. A method for identifying and producing a protease capable of cleaving the soluble p55 TNF-R from cell-bound TNF-R, comprising screening for a ligand capable of binding to a peptide comprising residue 202–211 of SEQ ID NO:2 except for the deletion of residue 202, the deletion of residues 202 and 203, the deletion of residues 203 and 204, the substitution of Pro at residue 202, 203 or 204, or the substitution of Asp or Gly at residue 202;

identifying and characterizing a ligand found by said screening step to be capable of said binding;

determining whether said ligand is a protease capable of cleaving the soluble p55 TNF-R from the cell-bound TNF-R; and if said step establishes that said ligand is a protease capable of said cleaving, producing said protease in substantially isolated and purified form.

2. A method in accordance with claim 1, wherein the peptide used in said screening step has a sequence comprising residues 202–211 of SEQ ID NO:2 except for the deletion of residue 202.

3. A method in accordance with claim 1, wherein said peptide has a sequence comprising residues 202–211 of SEQ ID NO:2 except for the deletion of residues 202 and 203.

4. A method in accordance with claim 1, wherein said peptide has a sequence comprising residues 202–211 of SEQ ID NO:2 except for the deletion of residues 203 and 204.

5. A method in accordance with claim 1, wherein said peptide has a sequence comprising residues 202–211 of SEQ ID NO:2 except for the substitution of Pro at residue 202.

6. A method in accordance with claim 1, wherein said peptide has a sequence comprising residues 202–211 of SEQ ID NO:2 except for the substitution of Asp at residue 202.

7. A method in accordance with claim 1, wherein said peptide has a sequence comprising residues 202–211 of SEQ ID NO:2 except for the substitution of Gly at residue 202.

8. A method in accordance with claim 1, wherein said peptide has a sequence comprising residues 202–211 of SEQ ID NO:2 except for the substitution of Pro at residue 203.

9. A method in accordance with claim 1, wherein said peptide has a sequence comprising residues 202–211 of SEQ ID NO:2 except for the substitution of Pro at residue 204.

\* \* \* \* \*

SEQUENCE LISTING ( 1 ) GENERAL INFORMATION:

( i i i ) NUMBER OF SEQUENCES: 42

( 2 ) INFORMATION FOR SEQ ID NO:1:

( i ) SEQUENCE CHARACTERISTICS:
        ( A ) LENGTH: 2175 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 256..1620

( x i ) SEQUENCE DESCRIPTION: SEQ ID NO:1:

```
CGGCCCAGTG ATCTTGAACC CCAAAGGCCA GAACTGGAGC CTCAGTCCAG AGAATTCTGA        60

GAAAATTAAA GCAGAGAGGA GGGGAGAGAT CACTGGGACC AGGCCGTGAT CTCTATGCCC       120

GAGTCTCAAC CCTCAACTGT CACCCCAAGG CACTTGGGAC GTCCTGGACA GACCGAGTCC       180

CGGGAAGCCC CAGCACTGCC GCTGCCACAC TGCCCTGAGC CCAAATGGGG GAGTGAGAGG       240

CCATAGCTGT CTGGC ATG GGC CTC TCC ACC GTG CCT GAC CTG CTG CTG CCG       291
                Met Gly Leu Ser Thr Val Pro Asp Leu Leu Leu Pro
                 1               5                  10

CTG GTG CTC CTG GAG CTG TTG GTG GGA ATA TAC CCC TCA GGG GTT ATT        339
Leu Val Leu Leu Glu Leu Leu Val Gly Ile Tyr Pro Ser Gly Val Ile
         15                  20                  25

GGA CTG GTC CCT CAC CTA GGG GAC AGG GAG AAG AGA GAT AGT GTG TGT        387
Gly Leu Val Pro His Leu Gly Asp Arg Glu Lys Arg Asp Ser Val Cys
     30                  35                  40

CCC CAA GGA AAA TAT ATC CAC CCT CAA AAT AAT TCG ATT TGC TGT ACC        435
Pro Gln Gly Lys Tyr Ile His Pro Gln Asn Asn Ser Ile Cys Cys Thr
 45                  50                  55                  60

AAG TGC CAC AAA GGA ACC TAC TTG TAC AAT GAC TGT CCA GGC CCG GGG        483
Lys Cys His Lys Gly Thr Tyr Leu Tyr Asn Asp Cys Pro Gly Pro Gly
                 65                  70                  75

CAG GAT ACG GAC TGC AGG GAG TGT GAG AGC GGC TCC TTC ACC GCT TCA        531
Gln Asp Thr Asp Cys Arg Glu Cys Glu Ser Gly Ser Phe Thr Ala Ser
             80                  85                  90

GAA AAC CAC CTC AGA CAC TGC CTC AGC TGC TCC AAA TGC CGA AAG GAA        579
Glu Asn His Leu Arg His Cys Leu Ser Cys Ser Lys Cys Arg Lys Glu
         95                 100                 105

ATG GGT CAG GTG GAG ATC TCT TCT TGC ACA GTG GAC CGG GAC ACC GTG        627
Met Gly Gln Val Glu Ile Ser Ser Cys Thr Val Asp Arg Asp Thr Val
110                 115                 120

TGT GGC TGC AGG AAG AAC CAG TAC CGG CAT TAT TGG AGT GAA AAC CTT        675
Cys Gly Cys Arg Lys Asn Gln Tyr Arg His Tyr Trp Ser Glu Asn Leu
125                 130                 135                 140

TTC CAG TGC TTC AAT TGC AGC CTC TGC CTC AAT GGG ACC GTG CAC CTC        723
Phe Gln Cys Phe Asn Cys Ser Leu Cys Leu Asn Gly Thr Val His Leu
                145                 150                 155

TCC TGC CAG GAG AAA CAG AAC ACC GTG TGC ACC TGC CAT GCA GGT TTC        771
Ser Cys Gln Glu Lys Gln Asn Thr Val Cys Thr Cys His Ala Gly Phe
            160                 165                 170

TTT CTA AGA GAA AAC GAG TGT GTC TCC TGT AGT AAC TGT AAG AAA AGC        819
Phe Leu Arg Glu Asn Glu Cys Val Ser Cys Ser Asn Cys Lys Lys Ser
        175                 180                 185
```

```
CTG GAG TGC ACG AAG TTG TGC CTA CCC CAG ATT GAG AAT GTT AAG GGC        867
Leu Glu Cys Thr Lys Leu Cys Leu Pro Gln Ile Glu Asn Val Lys Gly
    190             195                 200

ACT GAG GAC TCA GGC ACC ACA GTG CTG TTG CCC CTG GTC ATT TTC TTT        915
Thr Glu Asp Ser Gly Thr Thr Val Leu Leu Pro Leu Val Ile Phe Phe
205             210                 215                 220

GGT CTT TGC CTT TTA TCC CTC CTC TTC ATT GGT TTA ATG TAT CGC TAC        963
Gly Leu Cys Leu Leu Ser Leu Leu Phe Ile Gly Leu Met Tyr Arg Tyr
                225                 230                 235

CAA CGG TGG AAG TCC AAG CTC TAC TCC ATT GTT TGT GGG AAA TCG ACA       1011
Gln Arg Trp Lys Ser Lys Leu Tyr Ser Ile Val Cys Gly Lys Ser Thr
            240                 245                 250

CCT GAA AAA GAG GGG GAG CTT GAA GGA ACT ACT ACT AAG CCC CTG GCC       1059
Pro Glu Lys Glu Gly Glu Leu Glu Gly Thr Thr Thr Lys Pro Leu Ala
        255                 260                 265

CCA AAC CCA AGC TTC AGT CCC ACT CCA GGC TTC ACC CCC ACC CTG GGC       1107
Pro Asn Pro Ser Phe Ser Pro Thr Pro Gly Phe Thr Pro Thr Leu Gly
270                 275                 280

TTC AGT CCC GTG CCC AGT TCC ACC TTC ACC TCC AGC TCC ACC TAT ACC       1155
Phe Ser Pro Val Pro Ser Ser Thr Phe Thr Ser Ser Ser Thr Tyr Thr
285             290                 295                 300

CCC GGT GAC TGT CCC AAC TTT GCG GCT CCC CGC AGA GAG GTG GCA CCA       1203
Pro Gly Asp Cys Pro Asn Phe Ala Ala Pro Arg Arg Glu Val Ala Pro
                305                 310                 315

CCC TAT CAG GGG GCT GAC CCC ATC CTT GCG ACA GCC CTC GCC TCC GAC       1251
Pro Tyr Gln Gly Ala Asp Pro Ile Leu Ala Thr Ala Leu Ala Ser Asp
            320                 325                 330

CCC ATC CCC AAC CCC CTT CAG AAG TGG GAG GAC AGC GCC CAC AAG CCA       1299
Pro Ile Pro Asn Pro Leu Gln Lys Trp Glu Asp Ser Ala His Lys Pro
        335                 340                 345

CAG AGC CTA GAC ACT GAT GAC CCC GCG ACG CTG TAC GCC GTG GTG GAG       1347
Gln Ser Leu Asp Thr Asp Asp Pro Ala Thr Leu Tyr Ala Val Val Glu
350                 355                 360

AAC GTG CCC CCG TTG CGC TGG AAG GAA TTC GTG CGG CGC CTA GGG CTG       1395
Asn Val Pro Pro Leu Arg Trp Lys Glu Phe Val Arg Arg Leu Gly Leu
365             370                 375                 380

AGC GAC CAC GAG ATC GAT CGG CTG GAG CTG CAG AAC GGG CGC TGC CTG       1443
Ser Asp His Glu Ile Asp Arg Leu Glu Leu Gln Asn Gly Arg Cys Leu
                385                 390                 395

CGC GAG GCG CAA TAC AGC ATG CTG GCG ACC TGG AGG CGG CGC ACG CCG       1491
Arg Glu Ala Gln Tyr Ser Met Leu Ala Thr Trp Arg Arg Arg Thr Pro
            400                 405                 410

CGG CGC GAG GCC ACG CTG GAG CTG CTG GGA CGC GTG CTC CGC GAC ATG       1539
Arg Arg Glu Ala Thr Leu Glu Leu Leu Gly Arg Val Leu Arg Asp Met
        415                 420                 425

GAC CTG CTG GGC TGC CTG GAG GAC ATC GAG GAG GCG CTT TGC GGC CCC       1587
Asp Leu Leu Gly Cys Leu Glu Asp Ile Glu Glu Ala Leu Cys Gly Pro
430                 435                 440

GCC GCC CTC CCG CCC GCG CCC AGT CTT CTC AGA TGAGGCTGCG CCCTGCGGGC     1640
Ala Ala Leu Pro Pro Ala Pro Ser Leu Leu Arg
445                 450                 455

AGCTCTAAGG ACCGTCCTGC GAGATCGCCT TCCAACCCCA CTTTTTTCTG GAAAGGAGGG     1700
GTCCTGCAGG GGCAAGCAGG AGCTAGCAGC CGCCTACTTG GTGCTAACCC CTCGATGTAC     1760
ATAGCTTTTC TCAGCTGCCT GCGCGCCGCC GACAGTCAGC GCTGTGCGCG CGGAGAGAGG     1820
TGCGCCGTGG GCTCAAGAGC CTGAGTGGGT GGTTTGCGAG GATGAGGGAC GCTATGCCTC     1880
ATGCCCGTTT TGGGTGTCCT CACCAGCAAG GCTGCTCGGG GGCCCTGGT TCGTCCCTGA      1940
GCCTTTTTCA CAGTGCATAA GCAGTTTTTT TTGTTTTTGT TTGTTTTGT TTGTTTTTA      2000
```

```
AATCAATCAT GTTACACTAA TAGAAACTTG GCACTCCTGT GCCCTCTGCC TGGACAAGCA      2060

CATAGCAAGC TGAACTGTCC TAAGGCAGGG GCGAGCACGG AACAATGGGG CCTTCAGCTG      2120

GAGCTGTGGA CTTTTGTACA TACACTAAAA TTCTGAAGTT AAAAAAAAAA AAAAA           2175
```

( 2 ) INFORMATION FOR SEQ ID NO:2:

( i ) SEQUENCE CHARACTERISTICS:
        ( A ) LENGTH: 455 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Gly Leu Ser Thr Val Pro Asp Leu Leu Leu Pro Leu Val Leu Leu
  1               5                  10                  15

Glu Leu Leu Val Gly Ile Tyr Pro Ser Gly Val Ile Gly Leu Val Pro
             20                  25                  30

His Leu Gly Asp Arg Glu Lys Arg Asp Ser Val Cys Pro Gln Gly Lys
         35                  40                  45

Tyr Ile His Pro Gln Asn Asn Ser Ile Cys Cys Thr Lys Cys His Lys
     50                  55                  60

Gly Thr Tyr Leu Tyr Asn Asp Cys Pro Gly Pro Gly Gln Asp Thr Asp
 65                  70                  75                  80

Cys Arg Glu Cys Glu Ser Gly Ser Phe Thr Ala Ser Glu Asn His Leu
                 85                  90                  95

Arg His Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
            115                 120                 125

Lys Asn Gln Tyr Arg His Tyr Trp Ser Glu Asn Leu Phe Gln Cys Phe
130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
            165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
            195                 200                 205

Gly Thr Thr Val Leu Leu Pro Leu Val Ile Phe Phe Gly Leu Cys Leu
210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
            245                 250                 255

Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
            275                 280                 285

Pro Ser Ser Thr Phe Thr Ser Ser Ser Thr Tyr Thr Pro Gly Asp Cys
            290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
            325                 330                 335
```

-continued

| Pro | Leu | Gln | Lys<br>340 | Trp | Glu | Asp | Ser | Ala<br>345 | His | Lys | Pro | Gln | Ser<br>350 | Leu | Asp |
| Thr | Asp | Asp<br>355 | Pro | Ala | Thr | Leu | Tyr<br>360 | Ala | Val | Val | Glu | Asn<br>365 | Val | Pro | Pro |
| Leu | Arg<br>370 | Trp | Lys | Glu | Phe | Val<br>375 | Arg | Arg | Leu | Gly | Leu<br>380 | Ser | Asp | His | Glu |
| Ile<br>385 | Asp | Arg | Leu | Glu | Leu<br>390 | Gln | Asn | Gly | Arg | Cys<br>395 | Leu | Arg | Glu | Ala | Gln<br>400 |
| Tyr | Ser | Met | Leu | Ala<br>405 | Thr | Trp | Arg | Arg | Arg<br>410 | Thr | Pro | Arg | Arg | Glu<br>415 | Ala |
| Thr | Leu | Glu | Leu<br>420 | Leu | Gly | Arg | Val | Leu<br>425 | Arg | Asp | Met | Asp | Leu<br>430 | Leu | Gly |
| Cys | Leu | Glu<br>435 | Asp | Ile | Glu | Glu | Ala<br>440 | Leu | Cys | Gly | Pro | Ala<br>445 | Ala | Leu | Pro |
| Pro | Ala | Pro<br>450 | Ser | Leu | Leu | Arg<br>455 | | | | | | | | | |

(2) INFORMATION FOR SEQ ID NO:3:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (ix) FEATURE:
        (D) OTHER INFORMATION: /note= hu p55 TNF-R receptor chimera C3

(xi) SEQUENCE DESCRIPTION: SEQ ID NO:3:

| Lys<br>1 | Leu | Cys | Leu | Pro<br>5 | Ser | Phe | Glu | Val | Trp<br>10 | Pro | Ser | Gly | Pro | Lys<br>15 | Ile |
| Pro | Ser | Ile | Ala | Thr<br>20 | | | | | | | | | | | |

(2) INFORMATION FOR SEQ ID NO:4:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (D) OTHER INFORMATION: /note= hu p55 TNF-R receptor chimera C4

(xi) SEQUENCE DESCRIPTION: SEQ ID NO:4:

| Lys<br>1 | Leu | Cys | Leu | Pro<br>5 | Ser | Phe | Ala | Thr |

(2) INFORMATION FOR SEQ ID NO:5:

(i) SEQUENCE CHARACTERISTICS:
        (A) LENGTH: 34 amino acids
        (B) TYPE: amino acid
        (C) STRANDEDNESS: single
        (D) TOPOLOGY: linear (ii) MOLECULE TYPE: peptide (ix) FEATURE:

( D ) OTHER INFORMATION: /note= hu p55 TNF-R receptor
chimera C5

( x i ) SEQUENCE DESCRIPTION: SEQ ID NO:5:

| Lys | Leu | Cys | Leu | Pro | Gln | Ile | Glu | Asn | Val | Lys | Gly | Thr | Glu | Asp | Ser |
|---|---|---|---|---|---|---|---|---|---|---|---|---|---|---|---|
| 1 | | | | 5 | | | | | 10 | | | | | 15 | |

| Gly | Thr | Ser | Phe | Glu | Val | Trp | Pro | Ser | Gly | Pro | Lys | Ile | Pro | Ser | Ile |
|---|---|---|---|---|---|---|---|---|---|---|---|---|---|---|---|
| | | | 20 | | | | | 25 | | | | | 30 | | |

Ala Thr ( 2 ) INFORMATION FOR SEQ ID NO:6:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( D ) OTHER INFORMATION: /note= hu p55 TNF-R receptor
chimera C6

( x i ) SEQUENCE DESCRIPTION: SEQ ID NO:6:

| Lys | Leu | Cys | Leu | Pro | Gln | Ile | Glu | Asn | Val | Lys | Gly | Thr | Glu | Asp | Ser |
|---|---|---|---|---|---|---|---|---|---|---|---|---|---|---|---|
| 1 | | | | 5 | | | | | 10 | | | | | 15 | |

| Gly | Thr | Ser | Phe | Ala | Thr |
|---|---|---|---|---|---|
| | | | 20 | | |

( 2 ) INFORMATION FOR SEQ ID NO:7:

( i ) SEQUENCE CHARACTERISTICS:
        ( A ) LENGTH: 34 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( D ) OTHER INFORMATION: /note= hu p55 TNF-R receptor
chimera C9

( x i ) SEQUENCE DESCRIPTION: SEQ ID NO:7:

| Cys | His | Leu | Cys | His | Ala | Asn | Cys | Thr | Tyr | Gly | Cys | Ala | Gly | Pro | Gly |
|---|---|---|---|---|---|---|---|---|---|---|---|---|---|---|---|
| 1 | | | | 5 | | | | | 10 | | | | | 15 | |

| Leu | Gln | Gly | Cys | Glu | Val | Trp | Pro | Ser | Gly | Pro | Lys | Ile | Pro | Ser | Ile |
|---|---|---|---|---|---|---|---|---|---|---|---|---|---|---|---|
| | | | 20 | | | | | 25 | | | | | 30 | | |

Ala Thr ( 2 ) INFORMATION FOR SEQ ID NO:8:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( D ) OTHER INFORMATION: /note= hu p55 TNF-R mutant
construct 170-179

( x i ) SEQUENCE DESCRIPTION: SEQ ID NO:8:

Gly Thr Thr Val
1

( 2 ) INFORMATION FOR SEQ ID NO:9:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( D ) OTHER INFORMATION: /note= hu p55 TNF-R mutant
            construct 170-174

( x i ) SEQUENCE DESCRIPTION: SEQ ID NO:9:

Gly Thr Glu Asp Ser Gly Thr Thr Val
    1                 5

( 2 ) INFORMATION FOR SEQ ID NO:10:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( D ) OTHER INFORMATION: /note= hu p55 TNF-R mutant
            construct 175-179

( x i ) SEQUENCE DESCRIPTION: SEQ ID NO:10:

Ile Glu Asn Val Lys Gly Thr Thr Val
    1                 5

( 2 ) INFORMATION FOR SEQ ID NO:11:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( D ) OTHER INFORMATION: /note= hu p55 TNF-R mutant
            construct 171-172

( x i ) SEQUENCE DESCRIPTION: SEQ ID NO:11:

Ile Val Lys Gly Thr Glu Asp Ser Gly Thr Thr Val
    1                 5                     10

( 2 ) INFORMATION FOR SEQ ID NO:12:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( D ) OTHER INFORMATION: /note= hu p55 TNF-R mutant
            construct 172-173

( x i ) SEQUENCE DESCRIPTION: SEQ ID NO:12:

Ile Glu Lys Gly Thr Glu Asp Ser Gly Thr Thr Val
    1                 5                     10

( 2 ) INFORMATION FOR SEQ ID NO:13:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( D ) OTHER INFORMATION: /note= hu p55 TNF-R mutant
            construct 173-174

( x i ) SEQUENCE DESCRIPTION: SEQ ID NO:13:

Ile  Glu  Asn  Gly  Thr  Glu  Asp  Ser  Gly  Thr  Thr  Val
    1                   5                        10

( 2 ) INFORMATION FOR SEQ ID NO:14:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( D ) OTHER INFORMATION: /note= hu p55 TNF-R mutant
            construct 174-175

( x i ) SEQUENCE DESCRIPTION: SEQ ID NO:14:

Ile  Glu  Asn  Val  Thr  Glu  Asp  Ser  Gly  Thr  Thr  Val
    1                   5                        10

( 2 ) INFORMATION FOR SEQ ID NO:15:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( D ) OTHER INFORMATION: /note= hu p55 TNF-R mutant
            construct 175-176

( x i ) SEQUENCE DESCRIPTION: SEQ ID NO:15:

Ile  Glu  Asn  Val  Lys  Glu  Asp  Ser  Gly  Thr  Thr  Val
    1                   5                        10

( 2 ) INFORMATION FOR SEQ ID NO:16:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( D ) OTHER INFORMATION: /note= hu p55 TNF-R mutant
            construct 176-177

( x i ) SEQUENCE DESCRIPTION: SEQ ID NO:16:

Ile  Glu  Asn  Val  Lys  Gly  Asp  Ser  Gly  Thr  Thr  Val
    1                   5                        10

( 2 ) INFORMATION FOR SEQ ID NO:17:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( D ) OTHER INFORMATION: /note= hu p55 TNF-R mutant
            construct 177-178

( x i ) SEQUENCE DESCRIPTION: SEQ ID NO:17:

```
Ile Glu Asn Val Lys Gly Thr Ser Gly Thr Thr Val
1               5                   10
```

( 2 ) INFORMATION FOR SEQ ID NO:18:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( D ) OTHER INFORMATION: /note= hu p55 TNF-R mutant
            construct 178-179

( x i ) SEQUENCE DESCRIPTION: SEQ ID NO:18:

```
Ile Glu Asn Val Lys Gly Thr Glu Gly Thr Thr Val
1               5                   10
```

( 2 ) INFORMATION FOR SEQ ID NO:19:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( D ) OTHER INFORMATION: /note= hu p55 TNF-R mutant
            construct 179-180

( x i ) SEQUENCE DESCRIPTION: SEQ ID NO:19:

```
Ile Glu Asn Val Lys Gly Thr Glu Asp Thr Thr Val
1               5                   10
```

( 2 ) INFORMATION FOR SEQ ID NO:20:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( D ) OTHER INFORMATION: /note= hu p55 TNF-R mutant
            construct 173

( x i ) SEQUENCE DESCRIPTION: SEQ ID NO:20:

```
Ile Glu Asn Lys Gly Thr Glu Asp Ser Gly Thr Thr Val
1               5                   10
```

( 2 ) INFORMATION FOR SEQ ID NO:21:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( D ) OTHER INFORMATION: /note= hu p55 TNF-R mutant
        construct E 171 A ( x i ) SEQUENCE DESCRIPTION: SEQ ID NO:21:

```
Ile Ala Asn Val Lys Gly Thr Glu Asp Ser Gly Thr Thr Val
1               5                   10
```

( 2 ) INFORMATION FOR SEQ ID NO:22:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( D ) OTHER INFORMATION: /note= hu p55 TNF-R mutant
        construct N 172 A ( x i ) SEQUENCE DESCRIPTION: SEQ ID NO:22:

```
Ile Glu Ala Val Lys Gly Thr Glu Asp Ser Gly Thr Thr Val
1               5                   10
```

( 2 ) INFORMATION FOR SEQ ID NO:23:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( D ) OTHER INFORMATION: /note= hu p55 TNF-R mutant
        construct V 173 A ( x i ) SEQUENCE DESCRIPTION: SEQ ID NO:23:

```
Ile Glu Asn Ala Lys Gly Thr Glu Asp Ser Gly Thr Thr Val
1               5                   10
```

( 2 ) INFORMATION FOR SEQ ID NO:24:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( D ) OTHER INFORMATION: /note= hu p55 TNF-R mutant
        construct NV 172-173 AA ( x i ) SEQUENCE DESCRIPTION: SEQ ID NO:24:

```
Ile Glu Ala Ala Lys Gly Thr Glu Asp Ser Gly Thr Thr Val
1               5                   10
```

( 2 ) INFORMATION FOR SEQ ID NO:25:

( i ) SEQUENCE CHARACTERISTICS:
       ( A ) LENGTH: 14 amino acids
       ( B ) TYPE: amino acid
       ( C ) STRANDEDNESS: single
       ( D ) TOPOLOGY: linear ( i i ) MOLECULE TYPE: peptide ( i x ) FEATURE:
       ( D ) OTHER INFORMATION: /note= hu p55 TNF-R mutant
           construct K 174 A ( x i ) SEQUENCE DESCRIPTION: SEQ ID NO:25:

Ile Glu Asn Val Ala Gly Thr Glu Asp Ser Gly Thr Thr Val
   1               5                   10

( 2 ) INFORMATION FOR SEQ ID NO:26:

( i ) SEQUENCE CHARACTERISTICS:
       ( A ) LENGTH: 14 amino acids
       ( B ) TYPE: amino acid
       ( C ) STRANDEDNESS: single
       ( D ) TOPOLOGY: linear ( i i ) MOLECULE TYPE: peptide ( i x ) FEATURE:
       ( D ) OTHER INFORMATION: /note= hu p55 TNF-R mutant
           construct G 175 A ( x i ) SEQUENCE DESCRIPTION: SEQ ID NO:26:

Ile Glu Asn Val Lys Ala Thr Glu Asp Ser Gly Thr Thr Val
   1               5                   10

( 2 ) INFORMATION FOR SEQ ID NO:27:

( i ) SEQUENCE CHARACTERISTICS:
       ( A ) LENGTH: 14 amino acids
       ( B ) TYPE: amino acid
       ( C ) STRANDEDNESS: single
       ( D ) TOPOLOGY: linear ( i i ) MOLECULE TYPE: peptide ( i x ) FEATURE:
       ( D ) OTHER INFORMATION: /note= hu p55 TNF-R mutant
           construct N 172 P ( x i ) SEQUENCE DESCRIPTION: SEQ ID NO:27:

Ile Glu Pro Val Lys Gly Thr Glu Asp Ser Gly Thr Thr Val
   1               5                   10

( 2 ) INFORMATION FOR SEQ ID NO:28:

( i ) SEQUENCE CHARACTERISTICS:
       ( A ) LENGTH: 14 amino acids
       ( B ) TYPE: amino acid
       ( C ) STRANDEDNESS: single
       ( D ) TOPOLOGY: linear ( i i ) MOLECULE TYPE: peptide ( i x ) FEATURE:
       ( D ) OTHER INFORMATION: /note= hu p55 TNF-R mutant
           construct V 173 P ( x i ) SEQUENCE DESCRIPTION: SEQ ID NO:28:

Ile Glu Asn Pro Lys Gly Thr Glu Asp Ser Gly Thr Thr Val
   1               5                   10

( 2 ) INFORMATION FOR SEQ ID NO:29:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( D ) OTHER INFORMATION: /note= hu p55 TNF-R mutant
            construct K 174 P ( x i ) SEQUENCE DESCRIPTION: SEQ ID NO:29:

Ile Glu Asn Val Pro Gly Thr Glu Asp Ser Gly Thr Thr Val
1                5                        10

( 2 ) INFORMATION FOR SEQ ID NO:30:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( D ) OTHER INFORMATION: /note= hu p55 TNF-R mutant
            construct G 175 P ( x i ) SEQUENCE DESCRIPTION: SEQ ID NO:30:

Ile Glu Asn Val Lys Pro Thr Glu Asp Ser Gly Thr Thr Val
1                5                        10

( 2 ) INFORMATION FOR SEQ ID NO:31:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( D ) OTHER INFORMATION: /note= hu p55 TNF-R mutant
            construct T 176 P ( x i ) SEQUENCE DESCRIPTION: SEQ ID NO:31:

Ile Glu Asn Val Lys Pro Pro Glu Asp Ser Gly Thr Thr Val
1                5                        10

( 2 ) INFORMATION FOR SEQ ID NO:32:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( D ) OTHER INFORMATION: /note= hu p55 TNF-R mutant
            construct E 177 P ( x i ) SEQUENCE DESCRIPTION: SEQ ID NO:32:

Ile Glu Asn Val Lys Pro Thr Pro Asp Ser Gly Thr Thr Val
1                5                        10

( 2 ) INFORMATION FOR SEQ ID NO:33:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( D ) OTHER INFORMATION: /note= hu p55 TNF-R mutant
            construct N 172 E ( x i ) SEQUENCE DESCRIPTION: SEQ ID NO:33:

```
Ile Glu Glu Val Lys Gly Thr Glu Asp Ser Gly Thr Thr Val
1               5                   10
```

( 2 ) INFORMATION FOR SEQ ID NO:34:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( D ) OTHER INFORMATION: /note= hu p55 TNF-R mutant
            construct N 172 D ( x i ) SEQUENCE DESCRIPTION: SEQ ID NO:34:

```
Ile Glu Asp Val Lys Gly Thr Glu Asp Ser Gly Thr Thr Val
1               5                   10
```

( 2 ) INFORMATION FOR SEQ ID NO:35:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( D ) OTHER INFORMATION: /note= hu p55 TNF-R mutant
            construct N 172 H ( x i ) SEQUENCE DESCRIPTION: SEQ ID NO:35:

```
Ile Glu His Val Lys Gly Thr Glu Asp Ser Gly Thr Thr Val
1               5                   10
```

( 2 ) INFORMATION FOR SEQ ID NO:36:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( D ) OTHER INFORMATION: /note= hu p55 TNF-R mutant
            construct N 172 I ( x i ) SEQUENCE DESCRIPTION: SEQ ID NO:36:

```
Ile Glu Ile Val Lys Gly Thr Glu Asp Ser Gly Thr Thr Val
1               5                   10
```

( 2 ) INFORMATION FOR SEQ ID NO:37:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( D ) OTHER INFORMATION: /note= hu p55 TNF-R mutant
            construct V 173 D ( x i ) SEQUENCE DESCRIPTION: SEQ ID NO:37:

```
Ile  Glu  Asn  Asp  Lys  Gly  Thr  Glu  Asp  Ser  Gly  Thr  Thr  Val
 1              5                        10
```

( 2 ) INFORMATION FOR SEQ ID NO:38:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( D ) OTHER INFORMATION: /note= hu p55 TNF-R mutant
            construct V 173 G ( x i ) SEQUENCE DESCRIPTION: SEQ ID NO:38:

```
Ile  Glu  Asn  Gly  Lys  Gly  Thr  Glu  Asp  Ser  Gly  Thr  Thr  Val
 1              5                        10
```

( 2 ) INFORMATION FOR SEQ ID NO:39:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( D ) OTHER INFORMATION: /note= hu p55 TNF-R mutant
            construct V 173 R ( x i ) SEQUENCE DESCRIPTION: SEQ ID NO:39:

```
Ile  Glu  Asn  Arg  Lys  Gly  Thr  Glu  Asp  Ser  Gly  Thr  Thr  Val
 1              5                        10
```

( 2 ) INFORMATION FOR SEQ ID NO:40:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( D ) OTHER INFORMATION: /note= hu p55 TNF-R mutant
            construct K 174 E ( x i ) SEQUENCE DESCRIPTION: SEQ ID NO:40:

```
Ile  Glu  Asn  Val  Glu  Gly  Thr  Glu  Asp  Ser  Gly  Thr  Thr  Val
 1              5                        10
```

( 2 ) INFORMATION FOR SEQ ID NO:41:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( D ) OTHER INFORMATION: /note= hu p55 TNF-R mutant construct K 174 Q ( x i ) SEQUENCE DESCRIPTION: SEQ ID NO:41:

Ile Glu Asn Val Gln Gly Thr Glu Asp Ser Gly Thr Thr Val
    1                5                      10

( 2 ) INFORMATION FOR SEQ ID NO:42:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( D ) OTHER INFORMATION: /note= hu p55 TNF-R mutant construct K 174 T ( x i ) SEQUENCE DESCRIPTION: SEQ ID NO:42:

Ile Glu Asn Val Thr Gly Thr Glu Asp Ser Gly Thr Thr Val
    1                5                      10